| United States Patent [19] | [11] Patent Number: 5,071,802 |
| Shimizu et al. | [45] Date of Patent: Dec. 10, 1991 |

[54] REGENERATION OF CATALYSTS BY BURNING IN THE PRESENCE OF ALCOHOLS

[75] Inventors: Shinkichi Shimizu, Hyogo; Takayasu Niwa, Osaka; Nobuyuki Abe, Nara; Masanori Doba, Osaka; Akira Iguchi, Kyoto; Hiroshi Ichihashi; Masaru Kitamura, both of Osaka, all of Japan

[73] Assignee: Sumitomo Chemical Co., Ltd., Osaka, Japan

[21] Appl. No.: 489,952

[22] Filed: Mar. 7, 1990

[30] Foreign Application Priority Data

Mar. 8, 1989 [JP] Japan ..................................... 1-57354
Oct. 20, 1989 [JP] Japan ..................................... 1-274000

[51] Int. Cl.$^5$ ......................... B01J 29/38; B01J 21/20; C07D 201/04; C07D 211/70
[52] U.S. Cl. ....................................... 502/38; 208/120; 208/135; 502/33; 502/41; 540/536; 546/348
[58] Field of Search ....................... 502/38, 41, 42, 43, 502/33, 516

[56] References Cited

U.S. PATENT DOCUMENTS

| 2,506,307 | 5/1950 | Martin ..................................... 502/41 |
| 2,763,601 | 9/1956 | Martin et al. ........................ 208/164 |
| 3,966,587 | 6/1976 | Rittensky et al. .................... 208/164 |
| 4,108,795 | 8/1978 | Hemler et al. ......................... 502/42 |
| 4,118,339 | 10/1978 | Latos ..................................... 502/42 |
| 4,248,782 | 2/1981 | Fuchs et al. ................. 260/239.3 A |
| 4,428,822 | 1/1984 | Jones ..................................... 502/41 |
| 4,627,911 | 12/1986 | Chen et al. .......................... 208/120 |

FOREIGN PATENT DOCUMENTS

| 764917 | 9/1971 | Belgium . |
| 0156226 | 11/1985 | European Pat. Off. . |
| 2641429 | 3/1978 | Fed. Rep. of Germany ........ 502/41 |
| 1159059A | 6/1989 | Japan . |

OTHER PUBLICATIONS

Catalytic Reaction–(G) in the third paragraph in p. 278 to p. 280, published Feb. 28, 1967 (with English translation).

*Primary Examiner*—Paul E. Konopka
*Attorney, Agent, or Firm*—Cushman, Darby & Cushman

[57] ABSTRACT

Carbonaceous materials deposited on solid catalysts and produced, for example, in Beckmann rearrangement in a gaseous phase are burned off by effecting the treatment in the presence of alcohols such as methanol or ethanol together with molecular oxygen-containing gas in order to regenerate the catalyst activity.

11 Claims, No Drawings

REGENERATION OF CATALYSTS BY BURNING IN THE PRESENCE OF ALCOHOLS

The present invention relates to a process for regenerating solid catalysts which are employed for synthesis of organic compounds. The process for regeneration is conducted by removing carbonaceous materials deposited on the catalysts.

Synthesis of organic compounds in the presence of solid catalysts are employed in from industries in a large scale, such as petroleum refining industry or petrochemical industry, for example, cracking of crude oil or naphtha to chemical industires for preparing, for example, monomers for synthetic resins, dyes, agricultural chemicals or pharmaceuticals for synthesis of intermediate compounds of medicines. Reactions included in the synthesis are decomposition, alkylation, hydrogenation, reduction, oxidation, dehydrogenation, condensation, esterification, dehydration, hydration, isomerization, rearrangement, disproportionation, cyclization and/or halogenation.

Carbonaceous materials often deposit on catalysts in the reactions above, for instance, decompositions where radicals are ready to be produced, condensations or polymerizations where high molecular weight compounds are ready to be produced, reactions wherein unsaturated compounds and/or aromatic compounds are present, or reaction systems where catalysts have large affinity with products produced, for example, synthesis of nitrogen-containing organic compounds in the presence of solid acid catalysts. The carbonaceous materials are, for example, heavy complex materials produced from condensation or polymerization of principal products or by-products adsorbed on the catalysts, or cokes produced while dehydrogenation proceeds.

Carbonaceous materials coat the surface of catalysts as soon as they are produced, resulting in lowering catalytic activity, or decrease of selectivity of reactions by degradation of active sites. As deposition proceeds, carbonaceous materials accumulate among catalyst pellets until plugging of a catalyst bed or agglomeration or break of catalyst pellets are often brought about.

Decoking where the reaction is stopped and molecular oxygen-containing gas is passed through a catalyst bed at high temperature until carbonaceous materials deposited on catalyst pellets are burned, is usually conducted in order to regenerate catalysts (Catalysis Society of Japan, "Catalytic Engineering Course" Vol 7, "Catalytic reaction" (2), - oxidation, dehydrogenation, decomposition -, page 278, published on Feb. 28, 1967 by Chijin Shokan). Steam or inert gas may be accompanied by air or molecular oxygen-containing gas, in order to facilitate the removal of carbonaceous materials or control the burning. However, there are some carbonaceous materials left unremoved from the surface of catalyst by conventional techniques, with the result that catalytic activity is usually lowered. This is due to the fact that the regeneration is carried out at a temperature lower than the necessary temperature. It is hard from an economical point of view to increase temperature for regeneration compared with reaction temperature. Apparatuses made of specific heat-resistant materials or specific heating mediums are required for this effect. Heating mediums used in a fixed bed reaction which is effected in, for instance, multi-tube reactors where heating is made by heating mediums, have their own upper temperature limits. Reuse of catalysts which have not been subjected to sufficient regeneration is forced, when regeneration at high enough temperature is hardly effected by economical or technical reasons. One of problems encountered in such a reuse case is that catalytic activity is greatly smaller than initial activity and regeneration of the catalyst is hardly effected. Life of catalyst, i.e., a period of time from the first use to a refuse after several regenerations, is so short that a long running with the same sort of catalyst is hardly conducted.

Another problem is thermal degradation of catalysts, for example, chemical change of components, decrease in specific surface area, crystallization of amorphous components, disappearance of micropores, sintering of active ingredients, for example, dispersing metals, agglomeration of pellets for example, formation of large sized grains or no good fluidization in a fluidized catalyst bed, break of catalyst pellets, or vaporization of active ingredients. Optimum decoking temperature range is narrow.

The present invention resides in providing a regeneration process of solid catalysts which are used for synthesis of organic compounds, by which carbonaceous materials deposited on catalysts are sufficientiy taken off at a relatively low temperature.

The present invention also provides a regeneration process of solid catalysts by which carbonaceous materials deposited thereon are taken off and degradation of catalytic activity is prevented.

According to the present invention, carbonaceous materials deposited on catalysts are burned in the presence of air or molecular oxygen-containing gas, which is characterized by the fact that alcohols of the formula mentioned below are present together in the system:

$$R\text{—}OH \qquad (I)$$

wherein R stands for an alkyl group or a hydroxyalkyl group.

Symbol R includes $C_{1-6}$ groups, such as methyl, ethyl, n-propyl, iso-propyl, n-butyl, iso-butyl, tert-butyl, n-amyl, iso-amyl or n-hexyl groups or $C_{2-5}$ hydroxyalkyl groups such as hydroxyethyl, hydroxypropyl, hydroxybutyl or hydroxyhexyl groups.

Alcohols usable in the present invention are, for example, methanol, ethanol, n-propanol, iso-propanol, n-butanol, iso-butanol, tert-butanol, n-amyl alcohol, isoamyl alcohol, n-hexanol, ethylene glycol, 1,2-propanediol, 1,3-propanediol, 1,4-butanediol, 1,2-butanediol, 2,3-butanediol or 1,6-hexanediol. At least one of them is used. Preference is methanol and ethanol.

Catalysts are solid and include metal catalysts, metal oxide catalysts, silica-alumina, zeolite, metal sulfides, metal halides or combinations thereof. Active ingredients may be shaped without any additives, but supported on carriers or modified by ion-exchange. Metals include alkali metals, alkaline earth metals, copper, silver, zinc, cadmium, silicon, aluminium, gallium, rare earth metals, tin, lead, titanium, zirconium, hafnium, phosphorus, arsenic, antimony, bismuth, vanadium, niobium, tellurium, chromium, molybdenum, tungsten, manganese, iron, cobalt, nickel, thorium, uranium, ruthenium, rhodium, palladium or platinum. They may be in the complex form, for example, zeolite subjected to ion-exchange with various metal ions, metallic copper/-chromium oxide, copper oxide/chromium oxide, metallic copper/zinc oxide, copper oxide/zinc oxide or chromium oxide/zinc oxide catalysts or platinum catalyst supported on alumina.

Carbonaceous materials deposited on catalysts and to which the present invention is able to be applied are produced from, for example, cracking (for example, silica-alumina, zeolite, chromia-alumina or platinum catalysts), alkylation (for example, silica-alumina, zeolite, copper chloride, iron chloride or aluminium chloride catalysts), reduction (for example, nickel, cobalt, palladium, copper oxide/chromium oxide or platinum catalysts), oxidation (for example, vanadium oxide, molybdenum oxide, bismuth oxide, antimony oxide, silver, palladium or platinum catalysts), dehydrogenation (for example, zinc oxide or copper oxide catalysts), condensation (for example, silica-alumina or zeolite catalysts), esterification, dehydration, hydration, isomerization or rearrangement (for example, silica-alumina, zeolite, niobium oxide or solid acid catalysts), disproportionation (for example, tungsten oxide catalyst), cyclization (for example, zinc oxide, nickel or platinum catalyts), halogenation (for example, aluminium chloride or iron chloride catalyts) or hydrocarbon synthesis (silica-alumina or zeolite catalysts). Carbonaceous materials may also be those produced in reduction, dehydrogenation, dealkylation or cyclization where metallic copper/zinc oxide, metallic copper/chromium oxide, metallic nickel/metallic copper, metallic nickel/zinc oxide or zinc oxide/chromium oxide catalysts are employed. Preference is cracking or deparaffin reaction of crude oil, heavy oil, light oil or naphtha in the presence of silica-alumina or zeolite such as ZSM-5 catalysts, isomerization of alkyl aromatic hydrocarbons, alkylation of aromatic hydrocarbons, synthesis of pyridine bases, Beckmann rearrangement or synthesis of gasoline from methanol or synthesis of hydrocarbons, alcohols and/or glycols from $CO/H_2$.

An amount of carbonaceous materials deposited on catalysts is not able to be defined generally but is determined taking account of activity and/or selectivity of catalysts and period of time required for regeneration of catalysts. It is desirable to perform regeneration from economical and technical points of view when carbonaceous materials deposited reach usually 2-4% by weight on the basis of catalysts, since activity and selectivity of catalysts greatly decrease and operation of reactors is hardly controlled.

Any shape of catalyst pellets may be employed, for example, cylindrical, spherical or amorphous block shape. Catalysts may also be in the form of microbeads which are used in a Riser reactor or fluidized bed.

A manner to have alcohols accompanied by air or molecular oxygen-containing gas is that alcohols are vaporized in evaporators of alcohols and then the vaporized alcohols are mixed with air or molecular oxygen-containing gas before the mixture gas was fed to a catalyst bed. Alternatively, inert gas such as steam, nitrogen gas or carbon dioxide gas is allowed to be present at any stage before the mixture gas above is fed to the catalyst bed in order to control burning or avoid explosion.

Effect of alcohols added is acknowledged even if alcohols all are not completely burned. Ratio between alcohols and oxygen with or without inert gas is not critical. However, amount of alcohols should be selected taking into consideration efficiency of alcohols added and also a range where explosion occurs, preferably below the lower limit of the range. For example, amount of alcohols to be added is less than 6% by volume for methanol when it is used with air, or less than 10.5% by volume for ethanol when it is used with air.

Space velocity (SV) of gas for regeneration is not critical but usually not smaller than 100 $hr^{-1}$ taking efficiency into account.

Temperature for regeneration varies depending on catalysts and/or reactions, but usually is about 350° C. to about 600° C. Temperature of catalysts while regeneration is effected increases due to heat of combustion of alcohols. Composition of feed gas and/or flow rate of gas are changed, if desired, in a continuous or step-wise manner, in order to control catalyst bed temperature.

Increase of the temperature greatly varies depending on catalysts employed, form of carbonaceous materials deposited, concentrations of alcohols, oxygen, steam and/or other gas in feed gas, SV of gas, varieties of reactors, heating mediums for cooling of reactors and pre-heating temperature of feed gas. It is a matter of course that catalyst bed temperature should be kept below heat-resistant limit of apparatuses including reactors. It is not desirable to have catalyst bed temperature kept at unduly high temperature, taking heat degradation of catalysts into account.

Time required for regeneration varies depending on varieties of catalysts, form and amount of carbonaceous materials deposited, concentrations of alcohols, oxygen, steam and/or other gas in feed gas and/or temperature of a catalyst bed.

The present regeneration process is conducted independently alone. The process may be conducted in a combination manner with other processes. For instance, air or molecular oxygen-containing gas is charged at a high temperature in order to have almost carbonaceous materials burned off, temperature of a catalyst bed is changed if desired, and a mixture of air or molecular oxygen-containing gas with alcohols is further charged on the catalyst bed. Another manner is, for example, after a mixture of air or molecular oxygen-containing gas with alcohols is charged until carbonaceous materials are burned off, air or molecular oxygen-containing gas is charged on a catalyst bed.

The present process is able to remove carbonaceous materials deposited on catalysts at lower temperature than that in conventional processes, and catalytic activity is recovered. Regeneration is effected in remarkably shorter period of time than that of conventional processes effected at the same temperature. It is greatly advantageous for materials for apparatuses, heating cost and other economical points that regeneration of catalysts is made at lower temperature. Life of catalysts is longer due to decrease of heat load.

The present process is applied to many processes mentioned above, but preferably to production of ε-caprolactam by Beckmann rearrangement of cyclohexanone oxime in gas phase or production of pyridines.

The present process is explained in more detail by the examples.

Synthesis of ε-caprolactam

EXAMPLE 1

Preparation of a catalyst

Tetraethylorthosilicate [$Si(OC_2H_5)_4$, 100 g, Al content: not more than 10 ppm], aqueous tetra n-propylammonium hydroxide (10% by weight) solution (224 g) and ethanol (60 g) were charged in an autoclave (1.5 l) made of stainless steel and stirred vigorously for 30 minutes. The mixture had pH 13. The autoclave was tightly sealed and dipped in an oil bath. Hydrothermal synthesis was carried out for 120 hours at 105° C. under stirring (not less than 400 rpm). Pressure in the autoclave was 2-3 Kg/cm². The content had pH 11.8 when the hydrothermal reaction was over. White solid product was collected by filtration and washed continuously with distilled water until pH of the filtrate was about 7. After the product was dried, it was calcined under air stream for 4 hours at 500° to 530° C. to obtain powdery white crystals (27 g). This was identified to be pentasil zeolite by an X ray diffractometer. Elemental assay by atomic absorption spectrometry gave 3 ppm of aluminium.

To the crystals (10 g) was added aqueous ammonium chloride (5% by weight) solution (100 g) and the crystal was subjected to an ion-exchange treatment for one hour at 50°-60° C., before it was filtered. After the ion-exchange treatment was repeated four times, the crystal was washed with distilled water until no Cl⁻ was detected, and dried at 120° C. for 16 hours. The thus obtained crystals of $NH_4^+$ form were shaped to particles of 24-48 mesh and then calcined in a nitrogen gas stream at 500° C. for one hour. The crystals were named as catalyst A.

Synthesis of ε-caprolactam

A reaction tube made of quartz glass (1 cm diameter) packed with the catalyst A (0.3 g, 0.5 ml) was preheated at 350° C. for one hour under a nitrogen stream. A solution of cyclohexanone oxime (8.0% by weight) in benzene was charged with a rate of 11.5 g/hr, keeping the temperature of the catalyst bed at 350° C. Space velocity (WHSV) was 3.1 hr⁻¹. Reaction product was trapped and collected every one hour under water-cooling and assayed by gas chromatography.

Result at one hour after the reaction started:
conversion: 100%
selectivity: 78%
Reaction was allowed to proceed. Result at 6 hours:
conversion: 97%
selectivity: 80%

Color of the catalyst after the reaction was over turned to black, due to deposition of carbonaceous materials.

Space velocity (WHSV), conversion of cyclohexanone oxime and selectivity of ε-caprolactam are calculated by the following formulas.

WHSV (hr⁻¹)=feeding rate of cyclohexanone
oxime (Kg/hr)/weight of catalyst (Kg)

Conversion (%) of cyclohexanone
oxime={(A−B)/A}×100

Selectivity (%) of
ε-caprolactam={C/(A−B)}×100 wherein A: starting cyclohexanone oxime fed (mol)
B: cyclohexanone oxime unaltered (mol) and
C: ε-caprolactam in product (mol)

Regeneration of catalyst

Regeneration of the catalyst above was conducted at 440° C. for 3 hours while methanol (0.15 g/hr) together with air (2.5 l/hr) were fed. SV at this time was 5200 hr⁻¹. Color of the catalyst was changed to white. Removal of carbonaceous materials was confirmed.

Second synthesis of ε-caprolactam

Synthesis of ε-caprolactam was continued under the same conditions as those before the regeneration was effected, in the presence of the catalyst which had been subjected to regeneration in the presence of methanol as above.

| | Results | |
| --- | --- | --- |
| | Time after the reaction started | |
| | 1 hour | 6 hours |
| conversion | 99.6% | 85% |
| selectivity | 80% | 78% |

COMPARISON EXAMPLE 1

Synthesis of ε-caprolactam was conducted for 6 hours in the presence of the catalyst A in the same manner as in Example 1, synthesis of ε-caprolactam.

Catalyst on which carbonaceous materials were deposited was subjected to regeneration at 440° C. for 3 hours in an air stream (2.5 l/hr). SV was 5000 hr⁻¹. Color of the catalyst after the regeneration was over was still black and almost all carbonaceous materials were left unremoved.

Synthesis of ε-caprolactam was continued in the presence of the catalyst which had been subjected to the regeneration above, under the same conditions as those in Example 1, second synthesis of ε-caprolactam.

| | Results | |
| --- | --- | --- |
| | Time after the reaction started | |
| | 1 hour | 6 hours |
| conversion | 96% | 60% |
| selectivity | 75% | 70% |

EXAMPLE 2

A reaction tube made of quartz glass (1 cm diameter) packed with the catalyst A (1.8 g) was preheated at 350° C. for one hour in a nitrogen stream. A solution of cyclohexanone oxime (8.0% by weight) in benzene was fed with a rate of 69.0 g/hr and reaction was conducted for 6 hours. WHSV was 3.1 hr⁻¹.

| Average result: | conversion: | 99% |
| --- | --- | --- |
| | selectivity: | 80% |

After the reaction was over, the catalyst was taken out of the reaction tube, well mixed and divided into 0.3 g each. One of catalysts divided (X) was subjected to regeneration wherein methanol (0.15 g/hr) with air (2.5 l/hr) were fed at 440° C. for 3 hours. SV was 5200 hr⁻¹.

Another catalyst was subjected to regeneration under the same conditions as in X except that ethanol (0.10 g/hr) with air (2.5 l/hr) were fed (SV=5100 hr⁻¹).

The other catalyst was subjected to regeneration under the same conditions as in X except that n-hexanol (0.10 g/hr) with air (2.5 l/hr) were fed (SV=5040 hr⁻¹).

Assay of carbon and nitrogen contained in the catalysts which had been subjected to regeneration above was effected with an oxygen-recycling combustion, automatic, high sensitive N and C assay apparatus. Results are given in Table 1. Assay of catalyst before regeneration is applied to and of catalyst which had been subjected to regeneration wherein air (2.5 (/hr) was fed without alcohols at 440° C. for 3 hours, was mentioned for reference.

TABLE 1

| alcohols | C and N contents in catalysts | |
|---|---|---|
| | C (% by weight) | N (% by weight) |
| before regeneration was applied to | 4.10 | 0.375 |
| regenerated without alcohol | 0.387 | 0.0587 |
| methanol | 0.049 | 0.0038 |
| ethanol | 0.053 | 0.0032 |
| n-hexanol | 0.161 | 0.0168 |

COMPARISON EXAMPLE 2

Air (2.5 l/hr) was passed at 520° C. for 3 hours through a reaction tube made of glass (1 cm diameter) packed with the catalyst (0.3 g) obtained after the synthesis of ε-caprolactam was over in Example 2, in order to effect regeneration. SV=5000 hr$^{-1}$. Color of the catalyst after the regeneration was over was black, so that carbonaceous materials were not sufficiently removed.

Subsequently, air (2.5 l/hr) was fed at SV=5000 hr$^{-1}$ for 3 hours at 560° C. to find that color of the catalyst turned to white.

EXAMPLE 3

Preparation of catalyst

Example 1 was repeated to prepare a catalyst which contained Al (3 ppm) and was referred to as "catalyst A*".

Synthesis of ε-caprolactam

Example 1 was repeated except that the catalyst A* (0.6 g, 1.0 ml) was used in place of the catalyst A and a solution of cyclohexanone oxime (8.0% by weight) in benzene was fed at a rate of 23.0 g/hr in place of 11.5 g/hr.

| | Result | |
|---|---|---|
| | Time after the synthesis started | |
| | 1 hour | 6 hours |
| conversion | 100% | 98.9% |
| selectivity | 80.0% | 80.0% |

After the synthesis was over, a part of the catalyst was taken out of the reactor, thoroughly mixed, and was assayed with the same apparatus as in Example 2.

| C | N |
|---|---|
| 4.73% by weight | 0.45% by weight |

Regeneration of the catalyst

Methanol (0.15 g/hr) with air (2.5 l/hr) were fed at 430° C. for 5 hours through the catalyst (0.5 g, 0.8 ml). SV=3200 hr$^{-1}$. Subsequently, air (2.5 l/hr, SV=3100 hr$^{-1}$) without methanol was fed at the same temperature as above for 2 hours. A part of the catalyst thus treated was taken out of the reactor and mixed thoroughly for assay of C and N with the same apparatus as of Example 2.

| C | N |
|---|---|
| 0.031% by weight | 0.0031% by weight |

Second synthesis of ε-caprolactam

The same synthesis of ε-caprolactam mentioned above was continued except that the regenerated catalyst as above (0.3 g) was used in place of the catalyst A* and a solution of cyclohexanone oxime (8.0 % by weight) in benzene was fed at a rate of 11.5 g/hr in place of 23.0 g/hr.

| | Result | |
|---|---|---|
| | Time after the synthesis started | |
| | 1 hour | 6 hours |
| conversion | 99.9% | 97.0% |
| selectivity | 80.0% | 79.0% |

Synthesis of pyridine bases

In the following examples 4, 5 and 6 and comparison examples 3 and 4, yield of products is calculated according to the formulas mentioned below on the basis of total number of carbon atoms in the starting compounds of aliphatic aldehydes.

$$\text{Yield of pyridine} = \frac{\text{Total number of C atoms in pyridine produced}}{\text{Total number of C atoms in the starting aldehydes}} \times 100\%$$

$$\text{Yield of } \alpha, \beta \text{ or } \gamma\text{-picoline} = \frac{\text{Total number of C atoms in } \alpha, \beta \text{ or } \gamma\text{-picoline produced}}{\text{Total number of C atoms in the starting aldehydes}} \times 100\%$$

EXAMPLE 4

ZSM-5 zeolite was prepared according to YASHIMA's process ("Shokubai" 23 (3), 232, 1981).

Solution A was prepared by mixing distilled water (433.4 g), aluminium sulfate (4.6 g), tetra-n-propylammonium bromide (55.8 g) and sulfuric acid (40 g).

Solution B was prepared by mixing distilled water (320 g) and sodium silicate (453 g).

Solution C was prepared by mixing distilled water (754 g) and sodium chloride (189 g).

Solution C was charged in an autoclave (3 l) made of stainless steel and solutions A and B were dropped while the solution C was vigorously stirred, so that pH of mixture was controlled to be kept at 9.5 to 11. The autoclave was tightly sealed and temperature was raised to 160° C. to effect hydrothermal reaction for 20 hours under stirring and under 5-6 Kg/cm$^2$ (gauge) by pressure. After the reaction was over, the autoclave was cooled to the ambient temperature and a product was subjected to repetition of steps of filtration and washing with water, until chloride ion in the filtrate was not more than 1 ppm. After the product was dried in air at 110° C. for 16 hours, the product was calcined in air at 530° C. for 4 hours, to obtain crystals (112 g). The crystals had the same X ray diffraction spectrum as ZSM-5

(Na+ form) zeolite mentioned in Japanese patent Kokoku 46-10064. Si/Al was 90.

The ZSM-5 (Na+ form) zeolite was treated with aqueous ammonium chloride (5% by weight) solution three times (one liter of the aqueous solution, each time) at 50° to 60° C. for one hour to effect ion-exchange and then subjected to repetition of steps of filtration and washing with water, until chloride ion in the filtrate was not more than 1 ppm. Drying the zeolite at 110° C. for 16 hours gave ZSM-5 (NH4+ form) crystals (106 g).

The zeolite (NH4+ form) (20 g) was subjected to ion-exchange at 80° C. for 2 hours with aqueous thallium nitrate (0.1M) solution (200 ml) and then washed several times with distilled water (total amount: 400 ml). After being dried at 110° C. for 16 hours, the zeolite was calcined in air at 530° C. for 4 hours to obtain ZSM-5 (Tl+ form, Tl content=3.0%).

(Synthesis of pyridine bases, regeneration of catalyst and subsequent repetition of a cycle of synthesis and regeneration of catalyst)

Through a reaction tube made of glass (12.6 mm diameter) packed with ZSM-5 (Tl+ form) and preheated at 450° C. was passed a mixture of preheated ammonia gas (4 mol) and vapor mixture of acetaldehyde (2 mol) and formaldehyde (40% by weight aqueous solution, 1 mol) with SV=1000 hr$^{-1}$. A reaction product was absorbed in water and then FID gas chromatography assay was effected.

Average values for three hours after the reaction started:

| Pyridine | α-picoline | β-picoline | γ-picoline |
|---|---|---|---|
| 63% | 6% | 9% | 3% |
| Total yield | 81% | | |

Catalyst was deep black colored due to carbonaceous materials deposited thereon. Firstly nitrogen (20 ml/min) with air (20 ml/min) were fed for 20 minutes through a reaction tube (450° C.), secondly air (40 ml/min) with nitrogen (20 ml/min) for 20 minutes, and thirdly air (200 ml/min) with nitrogen (20 ml/min) for 10 minutes, and fourthly methanol (8.6 mg/min) with air (200 ml/min) for 2 hours, for regeneration. SV=2700 hr$^{-1}$.

A cycle of the steps of synthesis and regeneration of catalyst was repeated.

At the 50th cycle, yields were

| Pyridine | α-picoline | β-picoline | γ-picoline | Total |
|---|---|---|---|---|
| 61% | 6% | 10% | 3% | 80% |

Color of the catalyst after being regenerated was almost white which was close to color of the fresh catalyst.

COMPARISON EXAMPLE 3

Example 4 was repeated except that air (200 ml/min) only was passed in place of methanol (8.6 mg/min) with air (200 ml/min). SV=2700 hr$^{-1}$.

A cycle of the synthesis and regeneration of catalyst was repeated. At the 30th cycle, yields were

| Pyridine | α-picoline | β-picoline | γ-picoline | Total |
|---|---|---|---|---|
| 55% | 6% | 10% | 3% | 74% |

Color of the catalyst after regeneration was over was brown. Brown color was deepened as the cycle was more.

EXAMPLE 5

ZSM-5 (Tl+ form) in example 4 which with an aqueous tetraammine palladium nitrate complex solution had been impregnated was dried at 110° C. for 16 hours and calcined in air at 530° C. for 4 hours to obtain a catalyst (Tl content: 3.0% by weight; Pd content: 0.01% by weight).

The same synthesis-regeneration cycle as in example 4 was conducted except that the above mentioned catalyst was used in place of the ZSM-5 (Tl+ form).

| | Results: | |
|---|---|---|
| | Cycle | |
| | 1st | 200th |
| Pyridine | 65% | 64% |
| α-picoline | 6 | 6 |
| β-picoline | 10 | 10 |
| γ-picoline | 3 | 3 |
| Total | 84 | 83 |

COMPARISON EXAMPLE 4

The same synthesis-regeneration cycle as in comparison example 3 was conducted except that the catalyst mentioned in example 5 was used in place of the ZSM-5 (Tl+ form).

Result at the 50th cycle

| Pyridine | α-picoline | β-picoline | γ-picoline | Total |
|---|---|---|---|---|
| 61% | 6% | 10% | 3% | 80% |

EXAMPLE 6

The same synthesis-regeneration cycle as in example 4 was repeated except that the catalyst mentioned in example 5 was used in place of the ZSM (Tl+ form) and ethylene glycol (6.2 mg/min) (SV=2700 hr$^{-1}$) was used in place of the methanol.

Result at the 100th cycle

| Pyridine | α-picoline | β-picoline | γ-picoline | Total |
|---|---|---|---|---|
| 64% | 6% | 10% | 3% | 83% |

Synthesis of gasoline from methanol (hereinafter referred to as MTG reaction)

EXAMPLE 7

ZSM-5 (NH4+ form, 20 g) prepared in example 4 was calcined in air at 530° C. for 4 hours to obtain ZSM-5 (H+ form).

MTG reaction was carried out according to U.S. Pat. No. 3,928,483. That is, methanol vapor was fed through a reaction tube (12.6 mm diameter) made of glass, packed with crystalline ZSM-5 (H+ form, 5 g) and heated at 325° C. SV=2000 hr$^{-1}$.

FID gas chromatographic assay of a product gave substantially the same result as the product mentioned in the above U.S. patent.

A catalyst after the reaction was effected for 8 hours was yellowish brown colored due to carbonaceous materials deposited thereon. Nitrogen and air (20 ml/min, each) were first passed for 30 minutes through the reaction tube held at 325° C., secondly nitrogen (20 ml/min) and air (50 ml/min) for 30 minutes, thirdly nitrogen (20 ml/min) and air (200 ml/min) for one hour and fourthly a mixture gas of methanol (8.6 mg/min) with air (200 ml/min) for 3 hours, for regeneration of the catalyst. SV=1800 hr$^{-1}$.

Eight repetition of the above reaction-regeneration cycle was made. Amount of carbonaceous materials deposited on the catalyst after the 8th cycle was over was observed with a thermobalance. The result is given in Table 2.

COMPARISON EXAMPLE 5

Example 7 was repeated except that air (200 ml/min, SV=1700 hr$^{-1}$) only was used in place of methanol (8.6 mg/min) and air (200 ml/min).

Amount of carbonaceous materials deposited on catalyst after 8th cycle of reaction-regeneration was over was observed with a thermobalance. The result is given in Table 2.

TABLE 2

| Amount of carbonaceous materials in catalyst (% by weight)* | |
|---|---|
| | (300–650° C.) |
| Example 7 | 0.3 |
| Comparison example 5 | 0.5 |

Note *under a stream of air; temperature increasing rate of a catalyst specimen after regeneration was over: 5° C./min.

EXAMPLE 8

ZSM-5 (NH$_4^+$ form) prepared in example 4 which with an aqueous tetraammine platinum nitrate complex solution had been impregnated was dried at 110° C. for 16 hours and then calcined in air at 530° C. for 4 hours to prepare a catalyst (Pt content: 0.01% by weight).

Cracking of n-decane was effected according to Applied Catalysis. 19, 101 (1985). That is, through a reaction tube (12.6 mm diameter) made of glass, packed with the catalyst above (5 g) and heated to 325° C. was passed n-decane vapor (SV=250 hr$^{-1}$). Assay of the product by FID gas chromatograph gave almost the same result mentioned in the above literature.

The catalyst after the reaction was effected for 8 hours was black colored with carbonaceous materials deposited thereon. Firstly, nitrogen and air (20 ml/min each) were fed for 30 minutes through the reaction tube held at 325° C., secondly nitrogen (20 ml/min) with air (50 ml/min) for 30 minutes, thirdly nitrogen (20 ml/min) with air (200 ml/min) for one hour and lastly a mixture gas of methanol (8.6 mg/min) and air (200 ml/min) for 3 hours, for regeneration. SV=1800 hr$^{-1}$.

Amount of carbonaceous materials deposited on a catalyst after 8th cycle of the reaction-regeneration above was over were observed with a thermobalance. The result is given in Table 3.

COMPARISON EXAMPLE 6

Example 8 was repeated except air (200 ml/min) only was used with SV=1700 hr$^{-1}$ in place of the mixture gas of methanol (8.6 mg/min) and air (200 ml/min).

Amount of carbonaceous materials deposited on a catalyst after 8th cycle of the reaction-regeneration was over were observed with a thermobalance. The result is given in Table 3.

TABLE 3

| Amount of carbonaceous materials in catalyst (% by weight)* | |
|---|---|
| | (300–650° C.) |
| Example 8 | 1.0 |
| Comparison example 6 | 1.2 |

Note *the same as in Table 2

We claim:

1. A method of regenerating a catalyst material which has been contaminated with carbonaceous material, said method consisting essentially of burning the carbonaceous material deposited on the catalyst in the presence of:
   (a) air or a molecular oxygen containing gas; and
   (b) an alcohol of formula R—OH wherein R is alkyl or hydroxyalkyl
   wherein the carbonaceous materials were produced in a Beckmann rearrangement effected in a gaseous phase, in the synthesis of pyridine bases or in the synthesis of gasoline from methanol and wherein the catalyst is selected from the group consisting of metal catalysts, metal oxide catalysts, silica-alumina catalysts, zeolite catalysts, metal sulfide catalysts, metal halide catalysts and combinations thereof.

2. A process according to claim 1 wherein symbol R of the formula (I) is a C$_{1-6}$ alkyl group or a C$_{2-5}$ hydroxyalkyl group.

3. A process according to claim 1 wherein the alcohol is at least one selected from methanol, ethanol, n-propanol, iso-propanol, n-butanol, iso-butanol, tert-butanol, n-amyl alcohol, iso-amyl alcohol, n-hexanol, ethylene glycol, 1,2-propanediol, 1,3-propanediol, 1,4-butanediol, 1,2-butanediol, 2,3-butanediol, and 1,6-hexanediol.

4. A process according to claim 3 wherein the alcohol is at least one selected from methanol, ethanol, n-hexanol and ethylene glycol.

5. A process according to claim 4 wherein the alcohol is methanol or ethanol.

6. A process according to claim 1 wherein an amount of the alcohol is less than lower explosive limit.

7. A process according to claim 1 wherein the catalyst is zeolite.

8. A process according to claim 1 wherein the carbonaceous materials are produced in Beckmann rearrangement effected in a gaseous phase.

9. A process according to claim 1 wherein the carbonaceous materials are produced in synthesis of pyridine bases.

10. A process according to claim 1 wherein the carbonaceous materials are produced in synthesis of gasoline from methanol.

11. A method of regenerating catalyst material, which has been contaminated with carbonaceous material generated during a Beckmann rearrangement effected in a gaseous phase, the synthesis of pyridine bases, or the synthesis of gasoline from methanol, which consists essentially of burning the carbonaceous material deposited on the catalyst in the presence of a media consisting essentially of:

(a) air or a molecular oxygen containing gas; and
(b) at least one vaporized alcohol of formula R—OH wherein R is $C_1$–$C_6$ alkyl or $C_2$–$C_6$ hydroxyalkyl wherein:
the catalyst is selected from the group consisting of metal catalysts, metal oxide catalysts, silica-alumina catalysts, zeolite catalysts, metal sulfide catalysts, metal halide catalysts and combinations thereof, and the amount of alcohol present is less than the lower explosive limit.

* * * * *

UNITED STATES PATENT AND TRADEMARK OFFICE
CERTIFICATE OF CORRECTION

PATENT NO. : 5,071,802

DATED : December 10, 1991

INVENTOR(S) : Shinkichi SHIMIZU et al

It is certified that error appears in the above-identified patent and that said Letters Patent is hereby corrected as shown below:

ON TITLE PAGE: Item [73] should read

SUMITOMO CHEMICAL CO., LTD., OSAKA, JAPAN;
KOEI CHEMICAL CO., LTD., OSAKA, JAPAN

Signed and Sealed this

Twenty-ninth Day of September, 1992

Attest:

DOUGLAS B. COMER

*Attesting Officer*        *Acting Commissioner of Patents and Trademarks*